US012673297B2

(12) United States Patent
Tian et al.

(10) Patent No.: US 12,673,297 B2

(45) Date of Patent: Jul. 7, 2026

(54) METHOD FOR PREPARING POROUS AROMATIC FRAMEWORK MEMBRANES BASED ON INORGANIC SALT TEMPLATE METHOD

(71) Applicant: Northeast Normal University, Changchun City (CN)

(72) Inventors: Yuyang Tian, Changchun City (CN); Mengxiao Sun, Changchun City (CN); Guangshan Zhu, Changchun City (CN)

(*) Notice: Subject to any disclaimer, the term of this patent is extended or adjusted under 35 U.S.C. 154(b) by 125 days.

(21) Appl. No.: 18/731,315

(22) Filed: Jun. 2, 2024

(65) Prior Publication Data

US 2024/0335795 A1 Oct. 10, 2024

(30) Foreign Application Priority Data

Oct. 30, 2023 (CN) ........................ 202311420099.6

(51) Int. Cl.

| | |
|---|---|
| ***B29C 67/20*** | (2006.01) |
| ***B01D 67/00*** | (2006.01) |
| ***B01D 71/60*** | (2006.01) |
| ***C07C 211/54*** | (2006.01) |
| ***C07C 215/74*** | (2006.01) |

(Continued)

(52) U.S. Cl.

CPC ....... *B01D 67/003* (2013.01); *B01D 67/0006* (2013.01); *B01D 71/60* (2013.01); *B29C 67/202* (2013.01); *C07C 211/54* (2013.01); *C07C 215/74* (2013.01); *C07D 231/12* (2013.01); *B01D 2323/081* (2022.08); *B01D 2323/12* (2013.01); *B01D 2323/219* (2022.08); *B01D 2323/24* (2013.01); *B01D 2323/56* (2022.08); *B82B 3/0033* (2013.01)

(58) Field of Classification Search

CPC ............................ B29C 67/202; B01D 67/003

USPC ............................................................ 264/49

See application file for complete search history.

(56) References Cited

U.S. PATENT DOCUMENTS 3,956,020 A * 5/1976 Weininger ................. C08J 9/26 521/61

4,954,381 A * 9/1990 Cabasso ............... B01D 67/003 428/116

(Continued)

FOREIGN PATENT DOCUMENTS

CN 111154074 A * 5/2020 ............ B01J 20/226

EP 2450390 A1 * 5/2012 ........ B01J 20/28042

*Primary Examiner* — Atul P. Khare

(57) ABSTRACT

The present disclosure relates to the field of porous material synthesis, and particularly to a method for preparing porous aromatic framework membranes based on an inorganic salt template method. It aims at the problem of difficulty of preparation of porous aromatic framework membranes in large scale and large size. It uses alkynyl-containing building units and bromine-containing building units as raw materials and obtains continuous, dense, defect-free porous aromatic framework membranes through Sonogashira-Hagihara coupling polymerization. It specifically successfully prepares porous aromatic framework nanosheets on an inorganic salt substrate, and then produces a centimeter-scale large size continuous porous aromatic framework membrane through self-assembly. The method has mild conditions, a simple preparation process, and it is easy to operate. The prepared membranes have high yield and large area, and meet the requirements of actual industrial production.

10 Claims, 6 Drawing Sheets

(51) Int. Cl.

| | |
|---|---|
| ***C07D 231/12*** | (2006.01) |
| *B01D 71/06* | (2006.01) |
| *B82B 3/00* | (2006.01) |

(56) References Cited

U.S. PATENT DOCUMENTS

| | | | | |
|---|---|---|---|---|
| 8,685,296 | B2 * | 4/2014 | Liu | A61L 27/50<br>264/344 |
| 2012/0323339 | A1 * | 12/2012 | Olalde Graells | C08J 9/26<br>521/88 |

* cited by examiner

METHOD FOR PREPARING POROUS AROMATIC FRAMEWORK MEMBRANES BASED ON INORGANIC SALT TEMPLATE METHOD

CROSS-REFERENCE TO RELATED APPLICATION

This application claims priority to Chinese Patent Application No. 202311420099.6, filed on Oct. 30, 2023 before the China National Intellectual Property Administration, the disclosure of which is incorporated herein by reference in entirety.

TECHNICAL FIELD

The present disclosure relates to the field of porous material synthesis, and in particular to a method for preparing porous aromatic framework membranes based on an inorganic salt template method.

BACKGROUND

Membrane separation technology has shown great potential in industrial production due to its advantages of high efficiency, easy operation, low energy consumption and environmental sustainability. Compared with traditional inorganic membranes and polymer membranes, organic porous membranes possess abundant microporous structure, which leads to broad application prospects in the field of separation.

Porous aromatic frameworks (PAFs) have the characteristics of high specific surface area, flexible structure modification, and excellent chemical stability, and these advantages can make the PAFs with unique properties. However, the synthesis of PAFs relies on kinetically irreversible organic coupling reactions. Thus, it is a great challenge to control the synthesis process of membrane molding. In addition, due to their highly cross-linked framework structures, it is currently not feasible to directly melt and cast PAFs into membrane, most PAF membranes are prepared as mixed membrane with powdered PAFs and polymers. Although the problem of polymer membrane degradation is solved, there are still defects in practical applications. For example, in gas separation or liquid separation, PAFs/polymer interface defects lead to low selectivity, and excess polymer can easily lead to reduced permeability. In contrast, preparing porous aromatic frameworks as continuous membranes and applying them to separation can overcome performance limitations and have clear application advantages.

The only reported method to prepare continuous PAF membranes relies on surface initiation strategy. The key to the success of surface initiation strategy is to modify the active sites. The active sites are functional groups involved in the coupling reaction of porous aromatic frameworks, such as halogenated aromatic hydrocarbons, or arynes. However, the selection of surface coupling agents containing such functional groups is limited and high cost. Only multi-step reactions and multiple modifications can achieve efficient high-density modification of active sites. Therefore it is difficult to prepare large-scale and large-size continuous PAF membranes.

SUMMARY

In view of the shortcomings of the above-mentioned existing technologies, the purpose of the present disclosure is to provide a method for preparing porous aromatic framework membranes based on an inorganic salt template method, to overcome the technical problem that it is currently difficult to prepare PAF membranes in large scale and large size. The method uses alkynyl-containing building units and bromine-containing building units as raw materials and obtains continuous, dense, defect-free porous aromatic framework membranes through Sonogashira-Hagihara coupling polymerization. The method has mild conditions, a simple preparation process, and it is easy to operate. The prepared membranes have high yield and large area, and meet the requirements of actual industrial production.

In order to achieve the above objectives, the technical solutions adopted in this application are:

The present disclosure provides a method for preparing a porous aromatic framework membrane based on an inorganic salt template method. It mainly provides three continuous PAF membranes grown on a NaCl substrate, named PAF-34M, PAF-317M, and PAF-318M, and the feasibility of the method is verified. PAF-34M is based on tris(4-ethynylphenyl)amine and 1,3,5-tribromobenzene as raw materials, PAF-317M is based on tris(4-ethynylphenyl)amine and 1,3,5-tribromobenzene-2,4,6-triol as raw materials, and PAF-318M is based on 1,4-dibromo-2-(methyl imidazole methyl ethyl)benzene and tris(4-ethynylphenyl)amine as raw materials. PAF-34M, PAF-317M, and PAF-318M are obtained through Sonogashira-Hagihara coupling polymerization. The reaction principle of the Sonogashira-Hagihara reaction is: the oxidative addition of bromine-containing building unit and tetrakis (triphenylphosphine) palladium, that is, Pd (0), is achieved, tris(4-ethynylphenyl)amine is activated under the action of cuprous iodide, followed by metal exchange, reduction and elimination to obtain poly-substituted alkynes, and Pd (0) is regenerated at the same time; the PAFM produced by this method is continuously dense and defect-free, and it is the simplest and most efficient method for continuous PAFM synthesis at present.

A method for preparing a porous aromatic framework membrane based on an inorganic salt template method, comprising steps:

- mixing an inorganic salt template, tris(4-ethynylphenyl) amine and a bromine-containing building unit, adding solvent and triethylamine, which provides an alkaline environment for the reaction system, continuing to add catalyst under nitrogen protection, mixing evenly to obtain a mixed solution; and,
- under nitrogen protection and liquid nitrogen, letting the mixed solution undergo a freeze-vacuum-thaw cycle, then reacting at 60-150° C. for 48-96 hours, and collecting a NaCl layer and removing inorganic salt from the NaCl layer to obtain porous aromatic framework nanosheets, and then processing the porous aromatic framework nanosheets with a pressure-assisted method to obtain a porous aromatic framework membrane,
- wherein, the bromine-containing building unit is a bromine-containing organic monomer, the alkynyl-containing building unit is an alkynyl-containing monomer, and the numbers of bromine and alkynyl in the monomers are both greater than 1. If the numbers of bromine and alkynyl are respectively equal to 1, these building units can also be used in this application as end-capping agents; if the numbers of bromine and alkynyl in the monomer are both greater than 1, the bromine-containing building unit and the alkynyl-containing building unit will polymerize.

According to some embodiments of the present disclosure, the bromine-containing building unit comprises 1,3,5-tribromobenzene, 1,3,5-tribromobenzene-2,4,6-triol, 1,4-dibromo-2-(methyl imidazole methyl ethyl)benzene, 1,3,5-tris(4-bromophenyl)benzene, tetrabromotetraphenylmethane, tris(4-(bromomethyl)phenyl)amine, 1,4-dibromobenzene, 2,4,6-tribromo-1,3,5-trimethylbenzene, tetra(4-bromomethylphenyl)ethylene, or 1,4-dibromo-2,5-diethylbenzene;

the alkynyl-containing building unit comprises tris(4-ethynylphenyl)amine, 1,3,5-tris(4-ethynylphenyl)benzene, 5,10,15,20-tetrakis(4-ethynyl phenyl porphyrin), 1,3,5-triethynylbenzene, 1,4-diethynylbenzene, 4,4'-diethynylbiphenyl, tetrakis(4-ethynylbenzene)methane, 1,3,6,8-tetraethynylpyrene, 3,3',5,5'-tetraethynyl-1,1'-biphenyl. The bromine-containing building unit, and alkynyl-containing building unit are not limited to these compounds disclosed in this application. As long as they are bromine-containing organic monomers and alkynyl-containing monomers, they can be used in this application.

According to some embodiments of the present disclosure, a ratio of a mass of the inorganic salt template, an amount of the alkynyl-containing building unit, to an amount of the bromine-containing building unit is (10-20) g:(0.005-0.02) mmol:(0.005-0.02) mmol, and the molar ratio of bromine to alkynyl group is 1:1.

According to some embodiments of the present disclosure, the inorganic salt template is selected from a group consisting of sodium chloride, potassium chloride, magnesium chloride, calcium chloride, aluminium chloride, sodium sulfate, magnesium sulfate, and potassium sulfate.

According to some embodiments of the present disclosure, the solvent is selected from toluene, mesitylene, o-dichlorobenzene, N,N'-dimethylformamide, N,N'-dimethylacetamide, tetrahydrofuran, dichloromethane, triethylamine, and ethylenediamine.

According to some embodiments of the present disclosure, if the bromine-containing building unit is selected from 1,3,5-tribromobenzene and the alkynyl-containing building unit is selected from tris(4-ethynylphenyl)amine, a reaction formula of the porous aromatic framework membrane is:

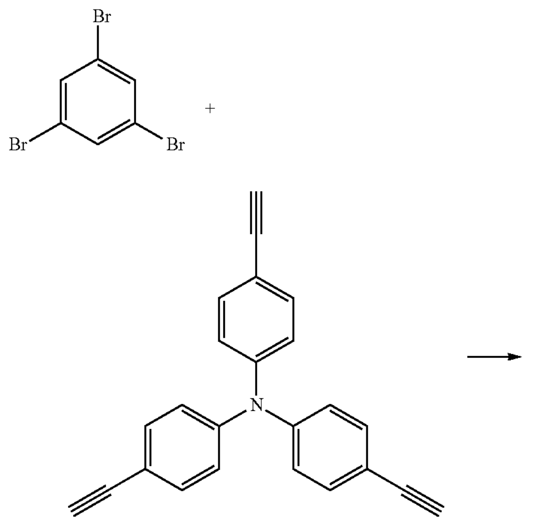

-continued

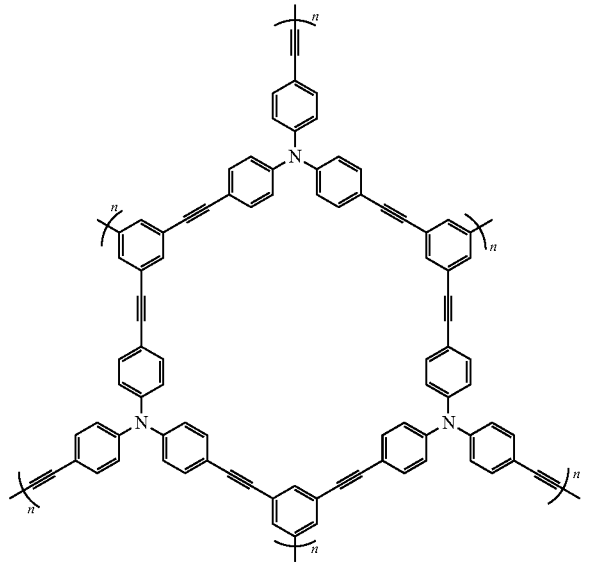

if the bromine-containing building unit is selected from 1,3,5-tribromobenzene-2,4,6-triol and the alkynyl-containing building unit is selected from tris(4-ethynylphenyl)amine, a reaction formula of the porous aromatic framework membrane is:

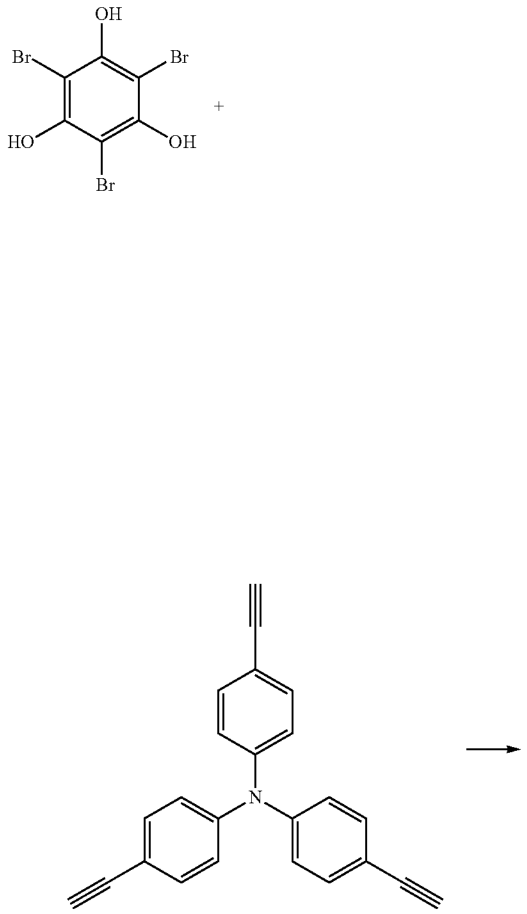

-continued
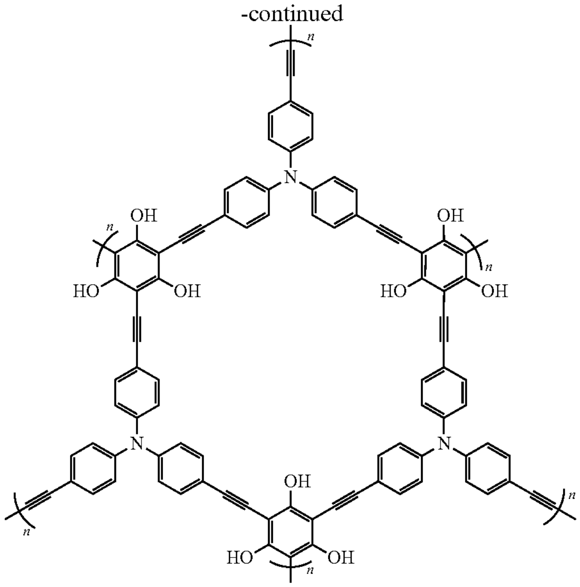
if the bromine-containing building unit is selected from 1,4-dibromo-2-(methyl imidazole methyl ethyl)benzene and the alkynyl-containing building unit is selected from tris(4-ethynylphenyl)amine, a reaction formula of the porous aromatic framework membrane is:
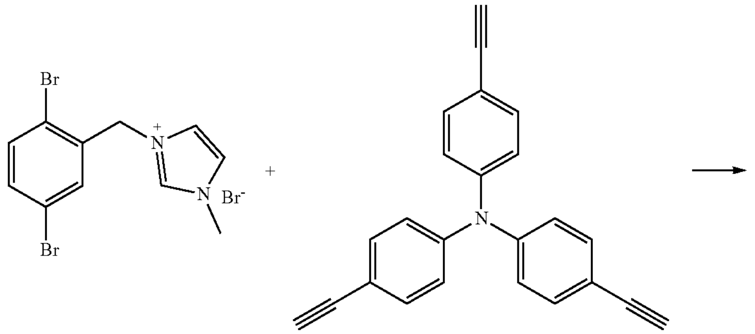

-continued

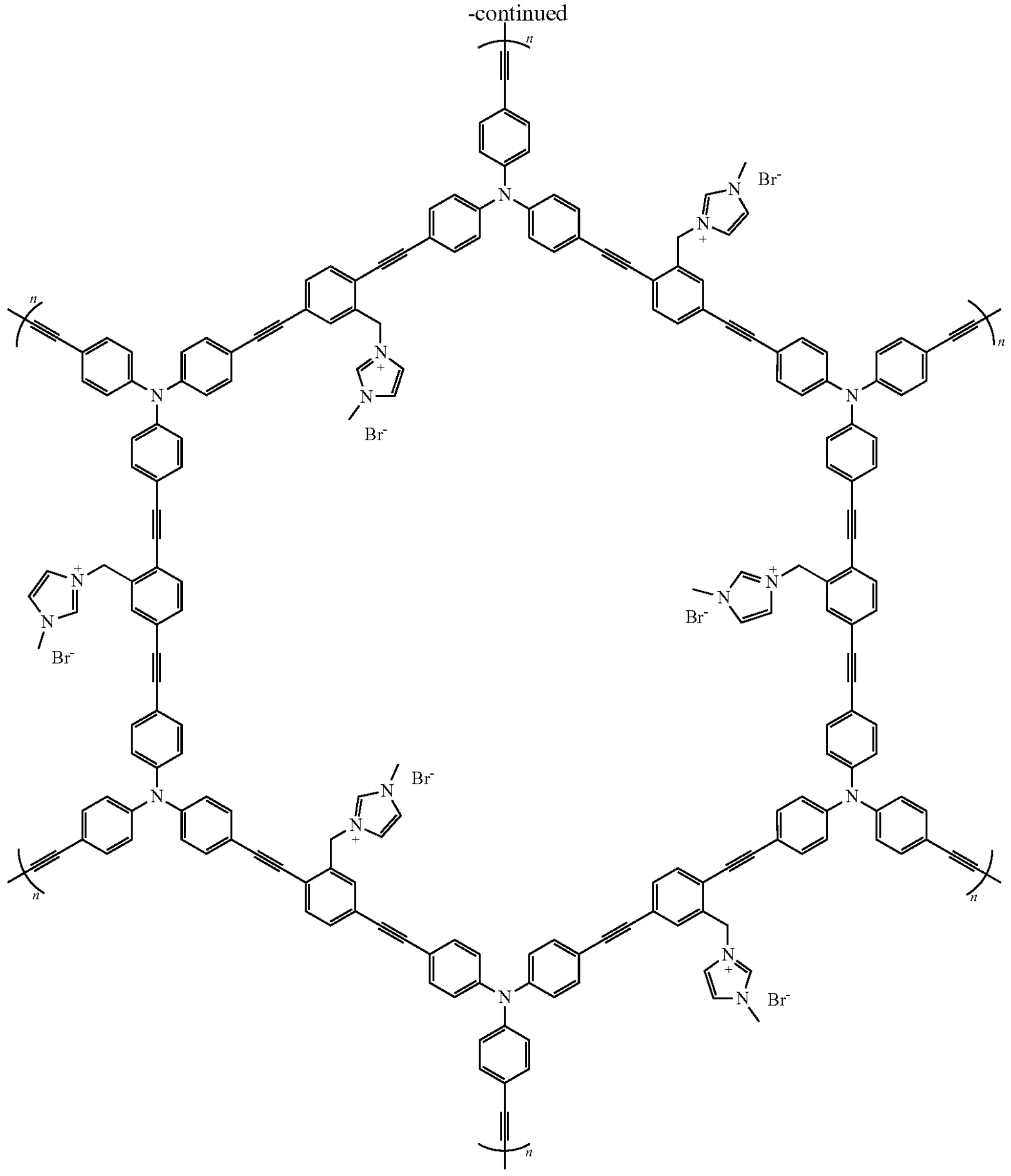

wherein, n≥1.

According to some embodiments of the present disclosure, a ratio of an amount of the bromine-containing building unit to a volume of triethylamine is 0.01 mmol:10-40 mL.

According to some embodiments of the present disclosure, the catalyst is composed of tetrakis (triphenylphosphine) palladium and cuprous iodide, and a mass ratio of the tetrakis (triphenylphosphine) palladium to the cuprous iodide is 10-15:2-5.

According to some embodiments of the present disclosure, a ratio of an amount of the bromine-containing building unit to a mass of the tetrakis (triphenylphosphine) palladium is 0.01 mmol:10-15 mg.

According to some embodiments of the present disclosure, the pressure-assisted method adopts a suction filtration operation.

According to some embodiments of the present disclosure, a method for removing the inorganic salt comprises: washing the inorganic salt layer by sequentially using chloroform, methanol, and water.

Compared with the existing technology, the beneficial effects of this application are:

I. The present disclosure provides a method for preparing a porous aromatic framework membrane based on an inorganic salt template method, that is, it intervenes in the growth space of PAF nanosheets by means of confinement, so that PAFs can only undergo polymerization reaction on the surface of the inorganic salt crystal, and after the polymerization reaction is completed, it adopts self-assembly to produce centimeter-scale large-sized continuous PAF membranes, which solved the problems of difficulty in preparing large-scale porous aromatic framework membranes, complicated preparation process and low yield. The PAF-317M, PAF-34M and PAF-318M prepared by the present disclosure have high continuity and large size.

II. The preparation process of the present disclosure has mild condition, simple preparation process, easy operation, the prepared membranes have high yield and large area, and it can meet actual industrial production requirements.

III. The present disclosure provides a method for preparing a porous aromatic framework membrane based on an inorganic salt template method. Specifically, it is a method for preparing porous aromatic framework nanosheets based on an inorganic salt template method. After further removing the inorganic salt template, and with the help of pressure-assisted method, the porous aromatic framework nanosheets are stacked, and centimeter-scale large-sized continuous porous aromatic framework membranes are prepared. Specifically, the present disclosure provides three porous aromatic framework continuous membranes, the three membranes are all prepared under the protection of protective atmosphere, using inorganic salt as a substrate, tris(4-ethynylphenyl)amine and 1,3,5-tribromobenzene as raw material, or tris(4-ethynylphenyl)amine and 1,3,5-tribromobenzene-2,4,6-triol as raw material, or 1,4-dibromo-2-(methyl imidazole methyl ethyl)benzene and tris(4-ethynylphenyl)amine as raw material, and adding catalyst for reaction, to prepare three kinds of porous aromatic framework nanosheets, which can be self-assembled to membranes by pressure-assisted method. It solves the technical problem of how to prepare large size porous aromatic framework membranes.

DETAILED DESCRIPTION OF EMBODIMENTS

Figure 1:
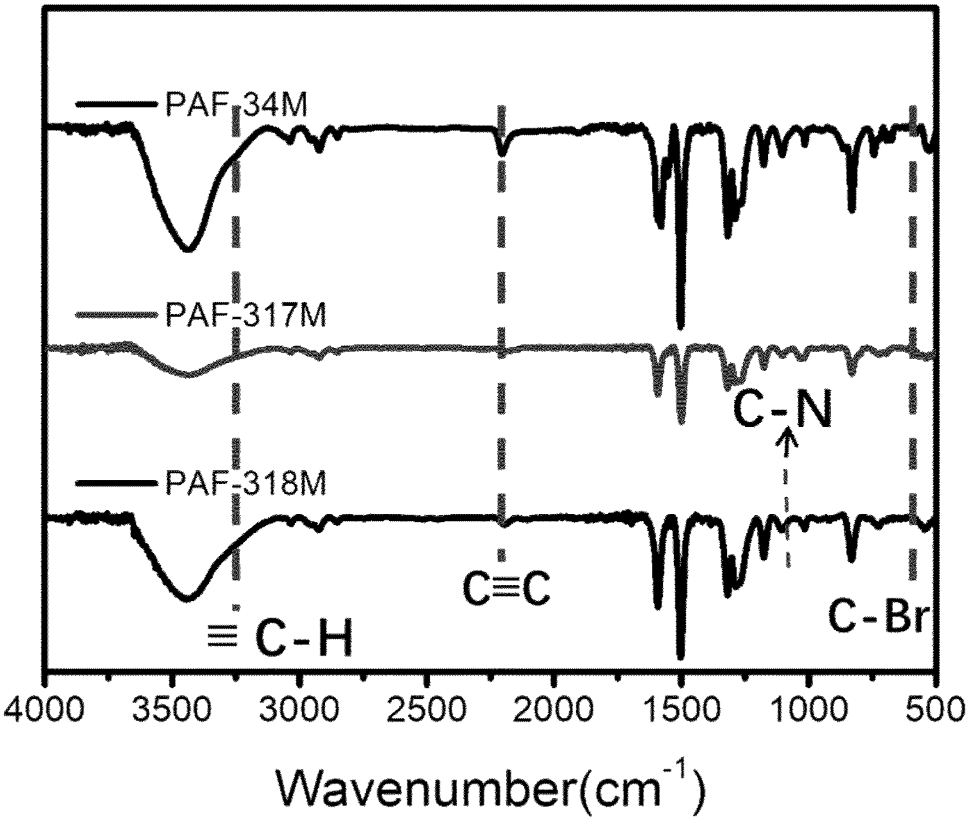
FIG. 1 shows Fourier transform infrared spectra of three porous aromatic framework membranes prepared in Examples 1, 5, and 9 of the present disclosure.

Specific embodiments of the present disclosure will be described in detail below in conjunction with the accompanying drawings, but it should be understood that the protection scope of the present disclosure is not limited by the specific embodiments. All other embodiments obtained by those of ordinary skill in the art based on the embodiments of the present disclosure without any creative work fall within the scope of protection of the present disclosure. The raw materials used in the present disclosure, if the manufacturer is not indicated, are all conventional products that can be purchased on the market.

In order to make the content of the present disclosure easier to understand, the technical solutions of the present disclosure will be further described below in conjunction with specific embodiments, but the present disclosure is not limited thereto.

In the present disclosure, 1,4-dibromo-2-(methylimidazolemethylethyl)benzene (1,4-dibromo-2-(methyl imidazole methyl ethyl)benzene) is a product prepared according to a reference literature. The DOI number of the reference literature is: 10.1002/anie.202113682;

Example 1

A method for preparing a porous aromatic framework membrane based on an inorganic salt template method. In this example, a porous aromatic framework membrane PAF-34M is prepared, it specifically includes the following steps:

Under a protective atmosphere of nitrogen, PAF-34M is prepared by using tris(4-ethynylphenyl)amine and 1,3,5-tribromobenzene as raw materials, adding them on a NaCl substrate, and polymerizing under a catalyst to form porous aromatic framework nanosheets.

The synthesis roadmap is:

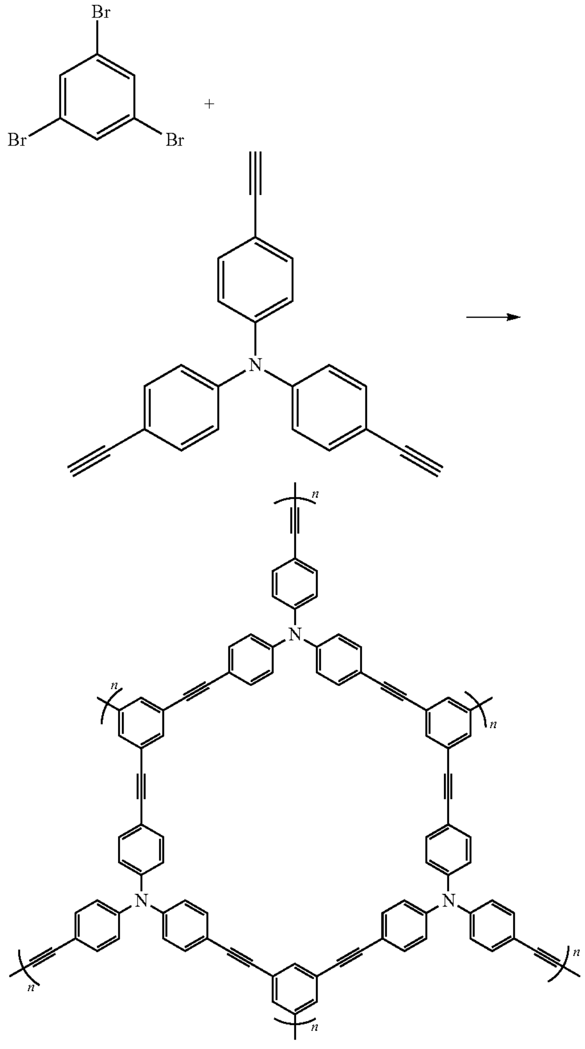

The specific synthesis method is as follows:

Weigh 15 g of NaCl, 31.7 mg (0.01 mmol) of tris(4-ethynylphenyl)amine and 31.5 mg (0.01 mmol) of 1,3,5-tribromobenzene, add them into a 100 mL double-necked flask, add 10 mL of toluene and 10 mL triethylamine (TEA, $Et_3N$), add 15 mg of tetrakis (triphenylphosphine) palladium and 5 mg of copper iodide under nitrogen protection to obtain a mixed solution. After ultrasonicating the mixed solution for 5 minutes, perform a freeze-pumping operation under nitrogen protection and liquid nitrogen, and undergo a freeze-vacuum-thaw cycle, then place it in a 150° C. oil bath to react for 48 hours; collect the NaCl layer, and then wash it with chloroform, methanol, and water respectively to obtain PAF-34 nanosheets, and then obtain continuous PAF-34M after suction filtration, and dry it in an oven at 100° C. for 10 hours.

Fourier transform infrared spectrum (IR) analysis is performed on the porous aromatic framework membrane (PAF-34M) prepared in Example 1. The characteristic peaks of the C—Br bond at 1075 $cm^{-1}$ and 600 $cm^{-1}$ disappear, and at the same time the strong absorption peak near 3300 $cm^{-1}$ related to the C—C stretching vibration of the alkynyl group disappears, indicating that the monomer has fully reacted; a low intensity peak is observed near 2200 $cm^{-1}$, it is due to the presence of the alkynyl C≡C in PAF-34M, which all proves the successful synthesis of PAF-34M.

Example 2

A method for preparing a porous aromatic framework membrane based on an inorganic salt template method. In this example, a porous aromatic framework membrane PAF-34M is prepared, it specifically includes the following steps:

Weigh 10 g of NaCl, 15.8 mg (0.005 mmol) of tris(4-ethynylphenyl)amine and 15.7 mg (0.005 mmol) of 1,3,5-tribromobenzene, add them into a 100 mL double-necked flask, add 5 mL of toluene and 5 mL of triethylamine (TEA, $Et_3N$), add 10 mg of tetrakis (triphenylphosphine) palladium and 2 mg of copper iodide under nitrogen protection to obtain a mixed solution. After ultrasonicating the mixed solution for 5 minutes, perform a freeze-pumping operation under nitrogen protection and liquid nitrogen, and undergo a freeze-vacuum-thaw cycle, then place it in a 60° C. oil bath to react for 96 hours; collect the NaCl layer, and then wash it with chloroform, methanol, and water respectively to obtain PAF-34 nanosheets, and then obtain continuous PAF-34M after suction filtration, and dry it in an oven at 100° C. for 10 hours.

Example 3

A method for preparing a porous aromatic framework membrane based on an inorganic salt template method. In this example, a porous aromatic framework membrane PAF-34M is prepared, it specifically includes the following steps:

Weigh 30 g of NaCl, 31.7 mg (0.02 mmol) of tris(4-ethynylphenyl)amine and 31.5 mg (0.02 mmol) of 1,3,5-tribromobenzene, add them into a 100 mL double-necked flask, add 40 mL of toluene and 40 mL triethylamine (TEA, $Et_3N$), add 15 mg (0.013 mmol) tetrakis (triphenylphosphine) palladium and 5 mg (0.013 mmol) copper iodide under nitrogen protection to obtain a mixed solution. After ultrasonicating the mixed solution for 5 minutes, perform a freeze-pumping operation under nitrogen protection and liquid nitrogen, and undergo a freeze-vacuum-thaw cycle, then place it in a 100° C. oil bath to react for 2 days; collect the NaCl layer, and then wash it with chloroform, methanol, and water respectively to obtain PAF-34 nanosheets, and then obtain continuous PAF-34M after suction filtration, and dry it in an oven at 100° C. for 10 hours.

Example 4

A method for preparing a porous aromatic framework membrane based on an inorganic salt template method. In this example, a porous aromatic framework membrane PAF-34M is prepared, it specifically includes the following steps:

Weigh 20 g of NaCl, 31.7 mg (0.01 mmol) of tris(4-ethynylphenyl)amine and 31.5 mg (0.01 mmol) of 1,3,5-tribromobenzene, add them into a 100 mL double-necked flask, add 20 mL of N,N-Dimethylformamide (DMF) and 20 mL triethylamine (TEA, $Et_3N$), add 13.8 mg (0.012 mmol) tetrakis (triphenylphosphine) palladium and 2.3 mg (0.012 mmol) copper iodide under nitrogen protection to obtain a mixed solution. After ultrasonicating the mixed solution for 5 minutes, perform a freeze-pumping operation under nitrogen protection and liquid nitrogen, and undergo a freeze-vacuum-thaw cycle, then place it in a 100° C. oil bath to react for 2 days; collect the NaCl layer, and then wash it with chloroform, methanol, and water respectively to obtain PAF-34 nanosheets, and then obtain continuous PAF-34M after suction filtration, and dry it in an oven at 100° C. for 10 hours.

Example 5

A method for preparing a porous aromatic framework membrane based on an inorganic salt template method. In this example, a porous aromatic framework membrane PAF-317M is prepared, it specifically includes the following steps:

Under a protective atmosphere of nitrogen, PAF-317M is prepared by using tris(4-ethynylphenyl)amine and 1,3,5-tribromobenzene-2,4,6-triol as raw materials, adding them to a substrate, and polymerizing under a catalyst to firm porous aromatic framework nanosheets (PAF-317).

The specific synthesis roadmap is:

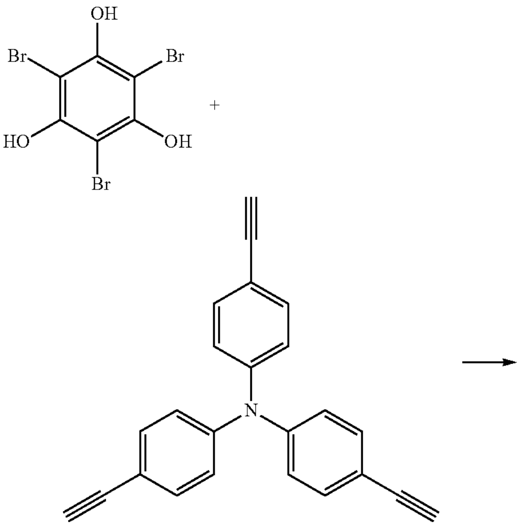

-continued

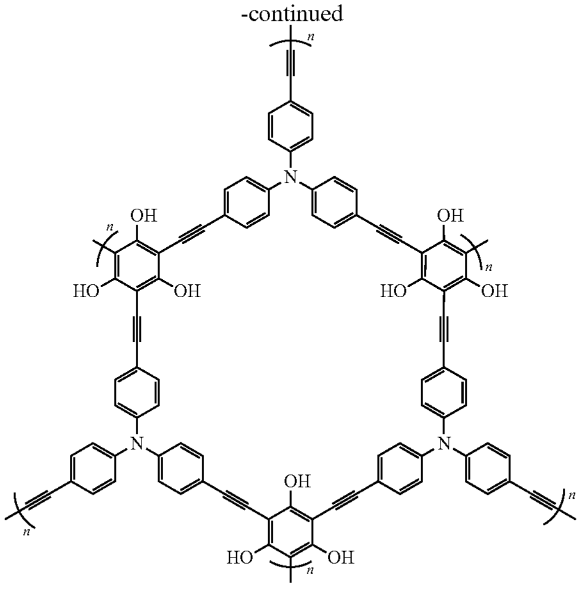

The specific synthesis method is as follows:

Weigh 15 g of NaCl, 31.7 mg (0.01 mmol) of tris(4-ethynylphenyl)amine and 36.3 mg (0.01 mmol) of 1,3,5-tribromobenzene-2,4,6-triol, add them into a 100 mL double-necked flask, add 10 mL of toluene and 10 mL of triethylamine (TEA, $Et_3N$), add 15 mg of tetrakis (triphenylphosphine) palladium and 5 mg of copper iodide under nitrogen protection to obtain a mixed solution. After ultrasonicating the mixed solution for 5 minutes, perform a freeze-pumping operation under nitrogen protection and liquid nitrogen, and undergo a freeze-vacuum-thaw cycle, then place it in a 150° C. oil bath to react for 48 hours; collect the NaCl layer, and then wash it with chloroform, methanol, and water respectively to obtain PAF-317 nanosheets, and then obtain continuous PAF-317M after suction filtration, and dry it in an oven at 100° C. for 10 hours.

Fourier transform infrared spectrum (IR) analysis is performed on the porous aromatic framework membrane (PAF-317M) prepared in Example 5. The characteristic peaks of the C—Br bond at 1075 $cm^{-1}$ and 600 $cm^{-1}$ disappear, and at the same time the strong absorption peak near 3300 $cm^{-1}$ related to the C—C stretching vibration of the alkynyl group disappears, indicating that the monomer has fully reacted; a low intensity peak is observed near 2200 $cm^{-1}$, it is due to the presence of the alkynyl C≡C in PAF-34M, and the broad stretching vibration peak of —OH at 3500 $cm^{-1}$ is still retained, which all proves the successful synthesis of PAF-317M.

Example 6

A method for preparing a porous aromatic framework membrane based on an inorganic salt template method. In this example, a porous aromatic framework membrane PAF-317M is prepared, it specifically includes the following steps:

Weigh 10 g of NaCl, 15.8 mg (0.005 mmol) of tris(4-ethynylphenyl)amine and 18.2 mg (0.005 mmol) of 1,3,5-tribromobenzene-2,4,6-triol, add them into a 100 mL double-necked flask, add 10 mL of toluene and 5 mL of triethylamine (TEA, $Et_3N$), add 10 mg of tetrakis (triphenylphosphine) palladium and 2 mg of copper iodide under nitrogen protection to obtain a mixed solution. After ultrasonicating the mixed solution for 5 minutes, perform a freeze-pumping operation under nitrogen protection and liquid nitrogen, and undergo a freeze-vacuum-thaw cycle, then place it in a 60° C. oil bath to react for 96 hours; collect the NaCl layer, and then wash it with chloroform, methanol, and water respectively to obtain PAF-317 nanosheets, and then obtain continuous PAF-317M after suction filtration, and dry it in an oven at 100° C. for 10 hours.

Example 7

A method for preparing a porous aromatic framework membrane based on an inorganic salt template method. In this example, a porous aromatic framework membrane PAF-317M is prepared, it specifically includes the following steps:

Weigh 20 g of NaCl, 63.4 mg (0.02 mmol) of tris(4-ethynylphenyl)amine and 72.6 mg (0.02 mmol) of 1,3,5-tribromobenzene-2,4,6-triol, add them into a 100 mL double-necked flask, add 15 mL of toluene and 15 mL of triethylamine (TEA, $Et_3N$), add 15 mg (0.013 mmol) of tetrakis (triphenylphosphine) palladium and 5 mg (0.013 mmol) of cuprous iodide under nitrogen protection to obtain a mixed solution. After ultrasonicating the mixed solution for 5 minutes, perform a freeze-pumping operation under nitrogen protection and liquid nitrogen, and undergo a freeze-vacuum-thaw cycle, then place it in a 100° C. oil bath to react for 2 days; collect the NaCl layer, and then wash it with chloroform, methanol, and water respectively to obtain PAF-317 nanosheets, and then obtain continuous PAF-317M after suction filtration, and dry it in an oven at 100° C. for 10 hours.

Example 8

A method for preparing a porous aromatic framework membrane based on an inorganic salt template method. In this example, a porous aromatic framework membrane PAF-317M is prepared, it specifically includes the following steps:

Weigh 20 g of NaCl, 31.7 mg (0.01 mmol) of tris(4-ethynylphenyl)amine and 36.3 mg (0.01 mmol) of 1,3,5-tribromobenzene-2,4,6-triol, add them into a 100 mL double-necked flask, add 20 mL N,N-Dimethylformamide (DMF) and 20 mL triethylamine (TEA, $Et_3N$), and add 13.8 mg (0.012 mmol) tetrakis (triphenylphosphine) palladium and 2.3 mg (0.012 mmol) of cuprous iodide under nitrogen protection to obtain a mixed solution. After ultrasonicating the mixed solution for 5 minutes, perform a freeze-pumping operation under nitrogen protection and liquid nitrogen, and undergo a freeze-vacuum-thaw cycle, then place it in a 100° C. oil bath to react for 48 h; collect the NaCl layer, and then wash it with chloroform, methanol, and water respectively to obtain PAF-317 nanosheets, and then obtain continuous PAF-317M after suction filtration, and dry it in an oven at 100° C. for 10 hours.

Example 9

A method for preparing a porous aromatic framework membrane based on an inorganic salt template method. In this example, a porous aromatic framework membrane PAF-318M is prepared, it specifically includes the following steps:

PAF-318M is prepared by using 1,4-dibromo-2-(methylimidazolemethylethyl)benzene and tris(4-ethynylphenyl)

amine as raw materials, adding them to a substrate, and polymerizing under a catalyst to form porous aromatic framework nanosheets.
The specific synthesis roadmap is:
The specific synthesis method is as follows:
Weigh 15 g of NaCl, 31.7 mg (0.01 mmol) of tris(4-ethynylphenyl)amine and 62.6 mg (0.01 mmol) of 1,4-dibromo-2-(methylimidazolemethylethyl)benzene, add
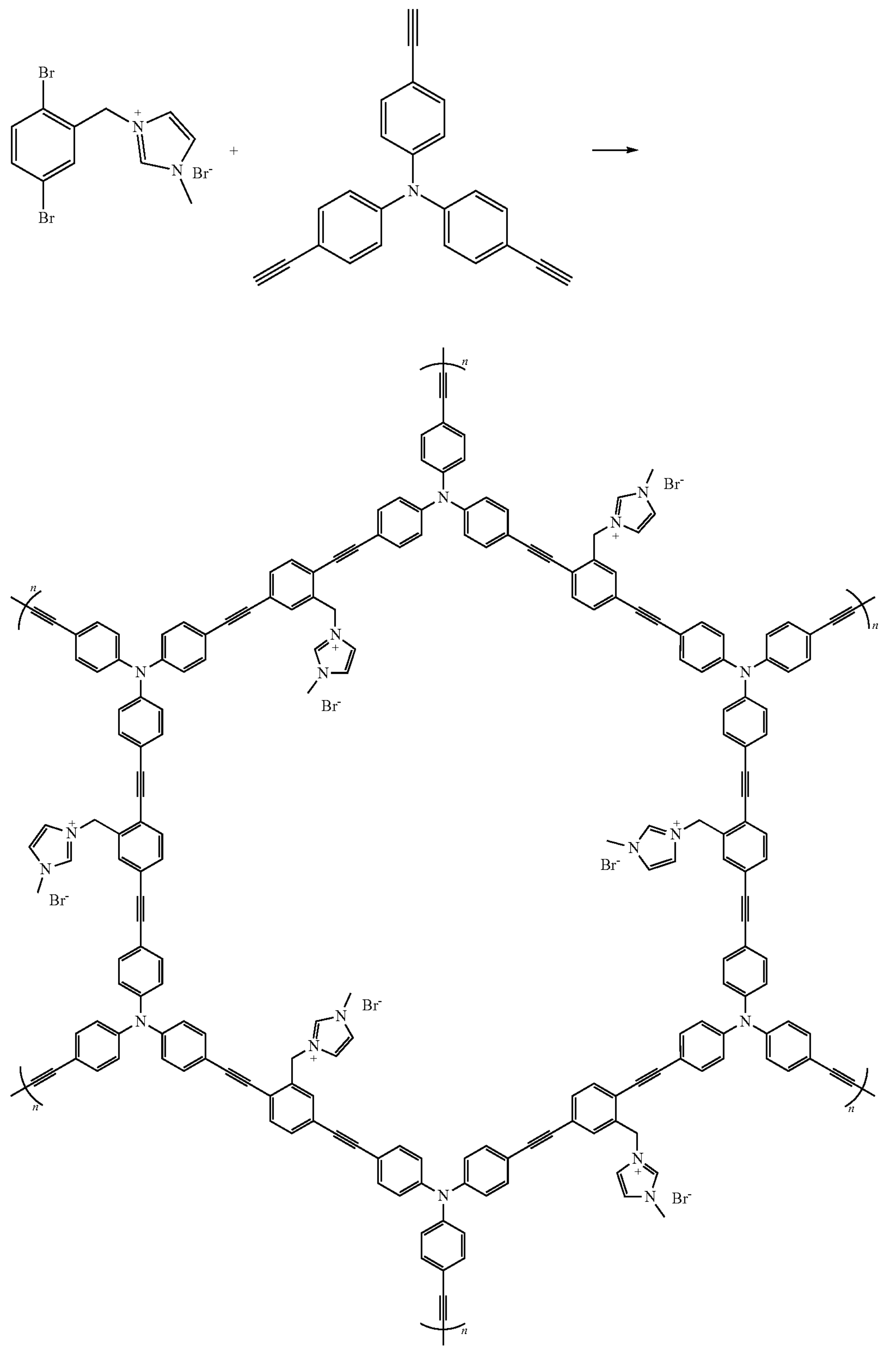

them into a 100 mL double-neck flask, add 10 mL toluene and 10 mL triethylamine (TEA, $Et_3N$), add 15 mg tetrakis (triphenylphosphine) palladium and 5 mg (0.012 mmol) cuprous iodide under nitrogen protection to obtain a mixed solution. After ultrasonicating the mixed solution for 5 minutes, perform a freeze-pumping operation under nitrogen protection and liquid nitrogen, and undergo a freeze-vacuum-thaw cycle, then place it in a 150° C. oil bath to react for 48 h; collect the NaCl layer, and then wash it with chloroform, methanol, and water respectively to obtain PAF-318 nanosheets, and then obtain continuous PAF-318M after suction filtration, and dry it in an oven at 100° C. for 10 hours.

Fourier transform infrared spectrum (IR) analysis is performed on the porous aromatic framework membrane (PAF-318M) prepared in Example 9. The characteristic peaks of the C—Br bond at 1075 $cm^{-1}$ and 600 $cm^{-1}$ disappear, and at the same time the strong absorption peak near 3300 $cm^{-1}$ related to the C—C stretching vibration of the alkynyl group disappears, indicating that the monomer has fully reacted; the characteristic stretching vibration peak at 1451 $cm^{-1}$ is attributed to the C═N bond in the imidazole ring, and the characteristic stretching vibration peak at 1398 $cm^{-1}$ is attributed to the C—H bond in the imidazole ring, the characteristic stretching vibration peak at 1109 $cm^{-1}$ is attributed to the C—N bond in the imidazole ring, which shows that the imidazole functional group is not destroyed during the polymerization process; a low-intensity peak is observed near 2200 $cm^{-1}$, this is due to the presence of alkynyl group C≡C in PAF-318M, which all proves the successful synthesis of PAF-318M.

Example 10

A method for preparing a porous aromatic framework membrane based on an inorganic salt template method. In this example, a porous aromatic framework membrane PAF-318M is prepared, it specifically includes the following steps:

Weigh 10 g of NaCl, 15.8 mg (0.005 mmol) of tris(4-ethynylphenyl)amine and 31.3 mg (0.005 mmol) of 1,4-dibromo-2-(methylimidazolemethylethyl)benzene, add them into a 100 mL double-neck flask, add 10 mL of toluene and 5 mL of triethylamine (TEA, $Et_3N$), add 10 mg of tetrakis (triphenylphosphine) palladium and 2 mg of cuprous iodide under nitrogen protection to obtain a mixed solution. After ultrasonicating the mixed solution for 5 minutes, perform a freeze-pumping operation under nitrogen protection and liquid nitrogen, and undergo a freeze-vacuum-thaw cycle, then place it in a 60° C. oil bath to react for 96 hours; collect the NaCl layer, and then wash it with chloroform, methanol, and water respectively to obtain PAF-318 nanosheets, and then obtain continuous PAF-318M after suction filtration, and dry it in an oven at 100° C. for 10 hours.

Example 11

A method for preparing a porous aromatic framework membrane based on an inorganic salt template method. In this example, a porous aromatic framework membrane PAF-318M is prepared, it specifically includes the following steps:

Weigh 20 g of NaCl, 63.4 mg (0.02 mmol) of tris(4-ethynylphenyl)amine and 125.2 mg (0.02 mmol) of 1,4-dibromo-2-(methylimidazolemethylethyl)benzene, add them into a 100 mL double-neck flask, add 15 mL of toluene and 15 mL of triethylamine (TEA, $Et_3N$), add 15 mg (0.013 mmol) of tetrakis (triphenylphosphine) palladium and 5 mg (0.013 mmol) of cuprous iodide under nitrogen protection to obtain a mixed solution. After ultrasonicating the mixed solution for 5 minutes, perform a freeze-pumping operation under nitrogen protection and liquid nitrogen, and undergo a freeze-vacuum-thaw cycle, then place it in a 100° C. oil bath to react for 2 days; collect the NaCl layer, and then wash it with chloroform, methanol, and water respectively to obtain PAF-318 nanosheets, and then obtain continuous PAF-318M after suction filtration, and dry it in an oven at 100° C. for 10 hours.

Example 12

A method for preparing a porous aromatic framework membrane based on an inorganic salt template method. In this example, a porous aromatic framework membrane PAF-318M is prepared, it specifically includes the following steps:

Weigh 20 g of NaCl, 31.7 mg (0.01 mmol) of tris(4-ethynylphenyl)amine and 62.6 mg (0.01 mmol) of 1,4-dibromo-2-(methylimidazolemethylethyl)benzene, add them into a 100 mL double-neck flask, add 20 mL of N,N-dimethylformamide (DMF) and 20 mL of triethylamine (TEA, $Et_3N$), and add 13.8 mg (0.012 mmol) of tetrakis (triphenylphosphine) palladium and 2.3 mg (0.012 mmol) of copper iodide under nitrogen protection to obtain a mixed solution. After ultrasonicating the mixed solution for 5 minutes, perform a freeze-pumping operation under nitrogen protection and liquid nitrogen, and undergo a freeze-vacuum-thaw cycle, then place it in a 100° C. oil bath to react for 48 h; collect the NaCl layer, and then wash it with chloroform, methanol, and water respectively to obtain PAF-318 nanosheets, and then obtain continuous PAF-318M after suction filtration, and dry it in an oven at 100° C. for 10 hours.

Example 13

Figure 6:
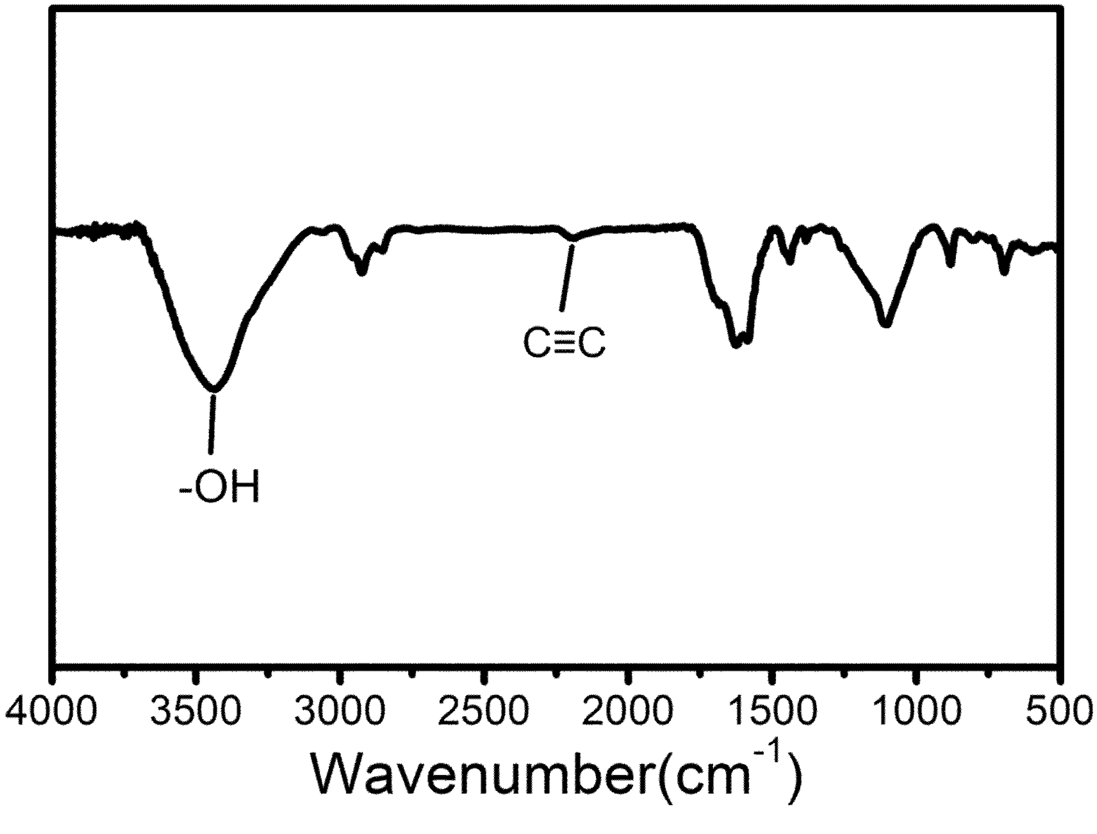
FIG. 6 shows Fourier transform infrared spectrum of the PAF membrane prepared in Example 13.

A method for preparing a porous aromatic framework membrane based on an inorganic salt template method, it specifically includes the following steps:

Weigh 20 g of $CaCl_2$, 0.01 mmol of 1,3,5-triethynylbenzene and 0.01 mmol of 2,4,6-tribromo-1,3,5-hydroxybenzene into a 100 mL double-necked flask, add 10 mL of toluene and 10 mL of triethylamine (TEA, $Et_3N$), add 13.8 mg (0.012 mmol) of tetrakis (triphenylphosphine) palladium and 2.3 mg (0.012 mmol) of cuprous iodide under nitrogen protection to obtain a mixed solution. After ultrasonicating the mixed solution for 5 minutes, perform a freeze-pumping operation under nitrogen protection and liquid nitrogen, and undergo a freeze-vacuum-thaw cycle, then place it in a 100° C. oil bath to react for 48 hours; collect the NaCl layer, and then wash it with chloroform, methanol, and water respectively, followed by suction filtration and dry it in an oven at 100° C. for 10 hours to obtain a porous aromatic framework membrane prepared based on the inorganic salt template method. The Fourier transform infrared characterization in FIG. 6 shows that the PAF membrane prepared in Example 13 was successfully synthesized.

Figure 2:
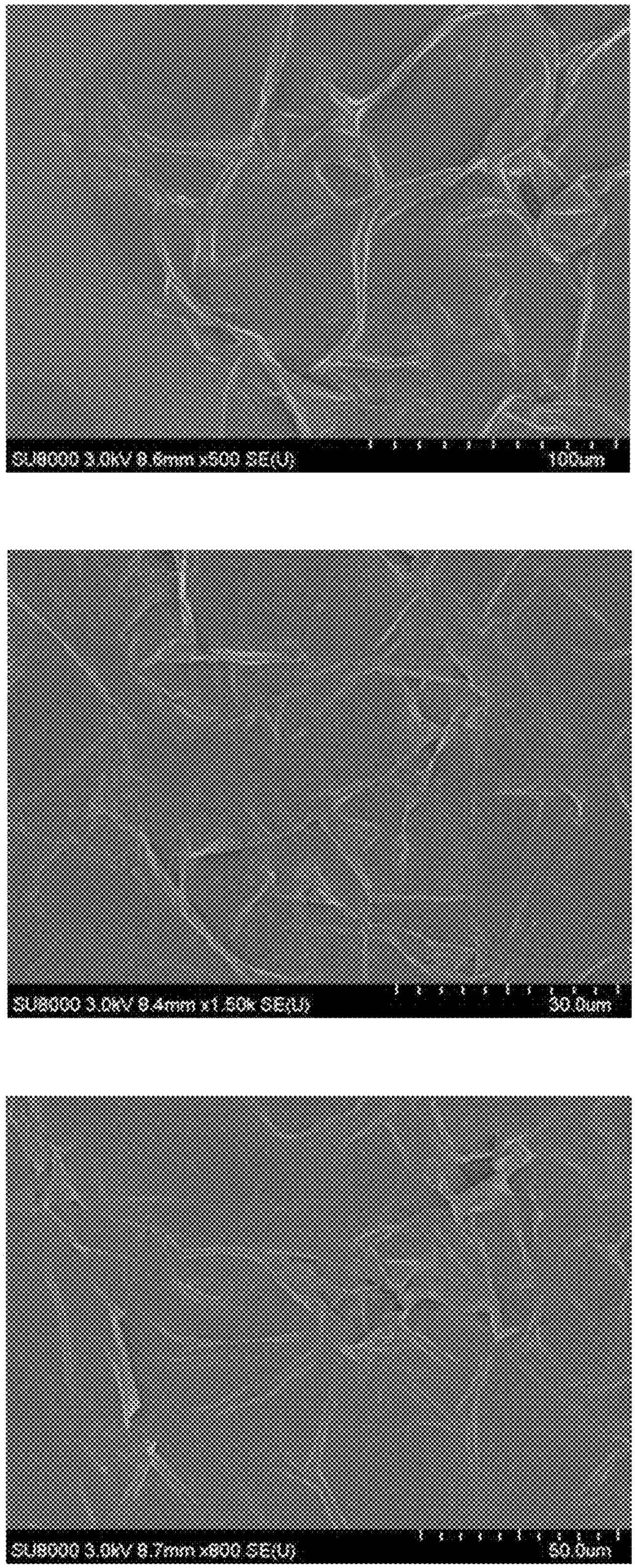
FIG. 2 is a scanning electron microscope characterization diagram of the porous aromatic framework membranes prepared in Examples 1, 5, and 9 of the present disclosure, wherein (a) is PAF-34M, (b) is PAF-317M, and (c) is PAF-318M.
Figure 3:
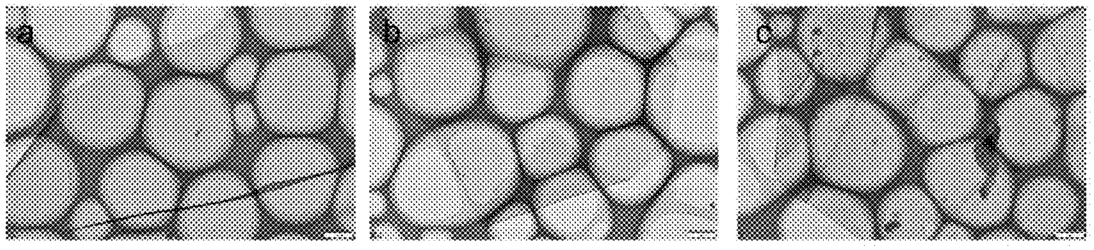
FIG. 3 is a transmission electron microscope characterization diagram of the porous aromatic framework membranes prepared in Examples 1, 5, and 9 of the present disclosure, wherein (a) is PAF-34M, (b) is PAF-317M, and (c) is PAF-318M.
Figure 4:
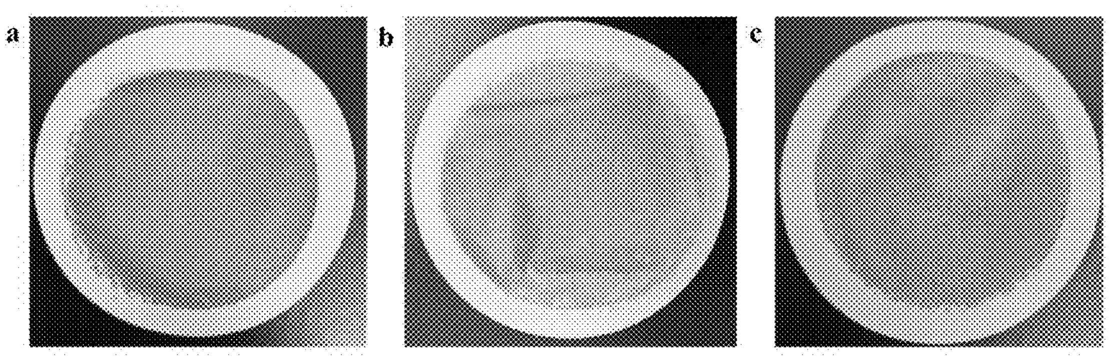
FIG. 4 shows optical photographs of the porous aromatic framework membranes prepared in Examples 1, 5, and 9 of the present disclosure, wherein (a) is PAF-34M, (b) is PAF-317M, and (c) is PAF-318M.

Next, we characterize the morphology of the porous aromatic framework membrane prepared in the above example. In FIG. 2, the scanning electron microscope of PAF-34M, PAF-317M, and PAF-318M shows that the surfaces of the three membranes are continuous and uniform, with no obvious holes or crack-like defects, and all have lamellar morphologies. The transmission electron microscopy characterization in FIG. 3 also shows a continuous and uniform film surface without obvious defects. As shown in FIG. 4, the optical photos confirm the successful synthesis of large-size PAF continuous membranes, this is a huge breakthrough in the field of PAF membrane synthesis.

Figure 5:
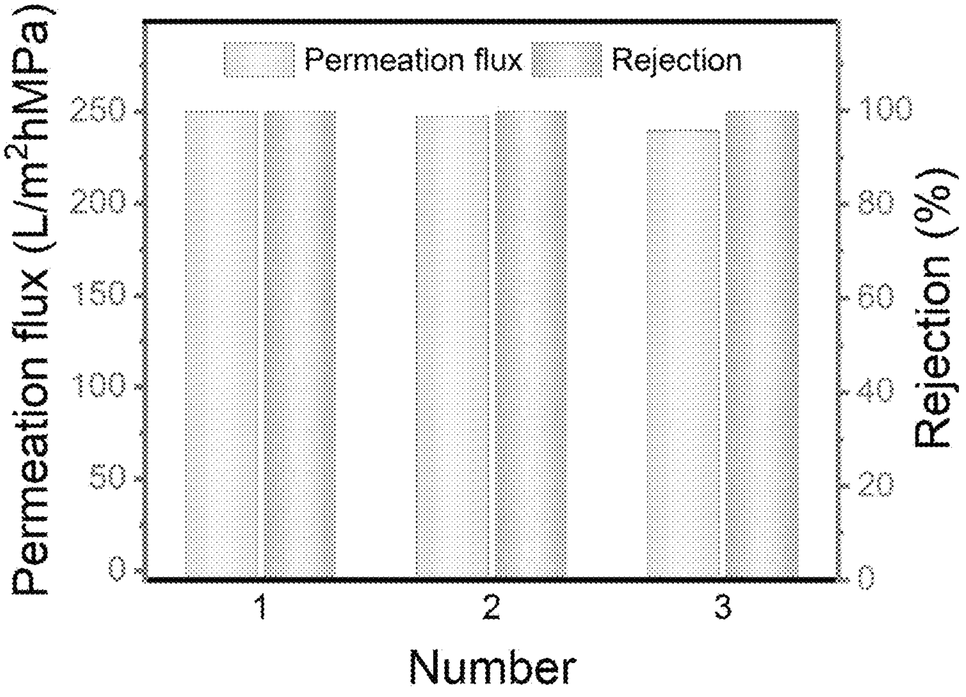
FIG. 5 shows the filtration performance of Congo red molecules using PAF-34M prepared in Example 1.

Congo red dye is an azo dye that is highly toxic and carcinogenic. Since Congo red dye has an aromatic nitro-complex benzene ring structure and is difficult to biodegrade, it would be of great benefit to human health if Congo red dye is effectively removed from wastewater. In order to verify that the membrane has a separation effect, a PAF-34 membrane was selected to measure the separation performance of the membrane by filtrating 100 mg/L Congo red aqueous solution for three filtration tests. The filtration test lasted for 6 hours in each cycle test, during which the ultraviolet-visible (UV-Vis) spectrum of the collected permeation fluid was measured every two hours to analyze the interception effect of the PAF-34 membrane on Congo red molecules. The results in FIG. 5 prove that at 0.2 MPa, the three permeation fluxes are 239.5 $L/m^2hMPa$, 250.0 $L/m^2hMPa$, and 247.5 $L/m^2hMPa$ respectively. The interception rate (rejection rate) of each filtration test remains above 99.99%. The high interception rate and high water permeation amount shows that the PAF continuous membrane synthesized based on this method has excellent separation performance.

Obviously, those skilled in the art can make various changes and modifications to the present disclosure without departing from the spirit and scope of the present disclosure. In this way, if these modifications and variations of the present disclosure fall within the scope of the claims of the present disclosure and equivalent technologies, the present disclosure is also intended to include these modifications and variations.

What is claimed is:

1. A method for preparing a porous aromatic framework membrane based on an inorganic salt template, comprising the following steps:

mixing an inorganic salt template, an alkynyl-containing building unit and a bromine-containing building unit, adding solvent and triethylamine to the mixture, and then adding catalyst under nitrogen protection, and mixing evenly to obtain a mixed solution; and under nitrogen protection and liquid nitrogen, subjecting the mixed solution to a freeze-vacuum-thaw cycle, then heating the mixed solution to 60-150° C. for 48-96 hours to yield an inorganic salt layer, collecting the inorganic salt layer, and removing inorganic salt from the inorganic salt layer to obtain porous aromatic framework nanosheets, and then processing the porous aromatic framework nanosheets via a pressure-assisted method to obtain a porous aromatic framework membrane, wherein the bromine-containing building unit is a bromine-containing organic monomer, the alkynyl-containing building unit is an alkynyl-containing monomer, and the numbers of bromine and alkynyl in the respective monomers are both greater than 1.

2. The method for preparing a porous aromatic framework membrane based on an inorganic salt template according to claim 1, wherein the bromine-containing building unit comprises 1,3,5-tribromobenzene, 1,3,5-tribromobenzene-2,4,6-triol, 1,4-dibromo-2-(methyl imidazole methyl ethyl) benzene, 1,3,5-tris (4-bromophenyl) benzene, tetrabromotetraphenylmethane, tris (4-(bromomethyl) phenyl) amine, 1,4-dibromobenzene, 2,4,6-tribromo-1,3,5-trimethylbenzene, tetra (4-bromomethylphenyl) ethylene, or 1,4-dibromo-2,5-diethylbenzene; and the alkynyl-containing building unit comprises tris (4-ethynylphenyl) amine, 1,3,5-tris (4-ethynylphenyl) benzene, 5,10,15,20-tetrakis (4-ethynyl phenyl porphyrin), 1,3,5-triethynylbenzene, 1,4-diethynylbenzene, 4,4'-diethynylbiphenyl, tetrakis (4-ethynylbenzene) methane, 1,3,6,8-tetraethynylpyrene, or 3,3',5,5'-tetraethynyl-1,l'-biphenyl.

3. The method for preparing a porous aromatic framework membrane based on an inorganic salt template according to claim 1, wherein a ratio of a mass of the inorganic salt template, an amount of the alkynyl-containing building unit, and an amount of the bromine-containing building unit is (10-20) g:(0.005-0.02) mmol:(0.005-0.02) mmol.

4. The method for preparing a porous aromatic framework membrane based on an inorganic salt template according to claim 1, wherein the inorganic salt template comprises a material selected from a group consisting of sodium chloride, potassium chloride, magnesium chloride, calcium chloride, aluminum chloride, sodium sulfate, magnesium sulfate, and potassium sulfate.

5. The method for preparing a porous aromatic framework membrane based on an inorganic salt template according to claim 1, wherein the solvent is selected from toluene, mesitylene, o-dichlorobenzene, N,N'-dimethylformamide, N,N'-dimethylacetamide, tetrahydrofuran, dichloromethane, triethylamine, and ethylenediamine.

6. The method for preparing a porous aromatic framework membrane based on an inorganic salt template according to claim 1:

wherein the bromine-containing building unit is 1,3,5-tribromobenzene and the alkynyl-containing building unit is tris (4-ethynylphenyl) amine to yield the following reaction formula of the porous aromatic framework membrane:

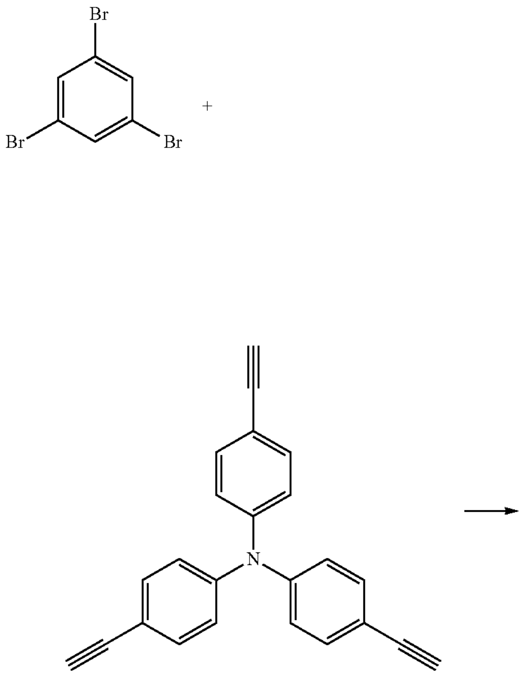

-continued

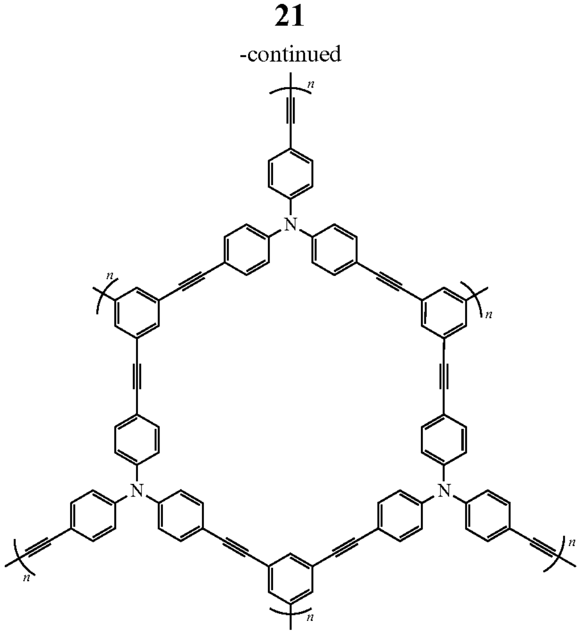

-continued

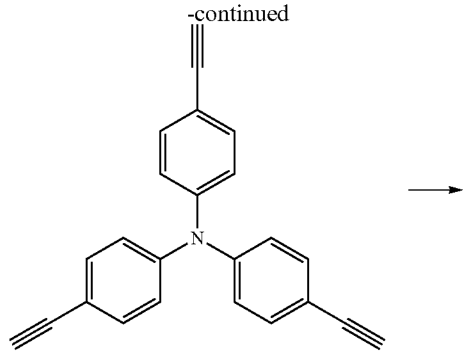

wherein the bromine-containing building unit is 1,3,5-tribromobenzene-2,4,6-triol and the alkynyl-containing building unit is tris (4-ethynylphenyl) amine to yield the following reaction formula of the porous aromatic framework membrane:

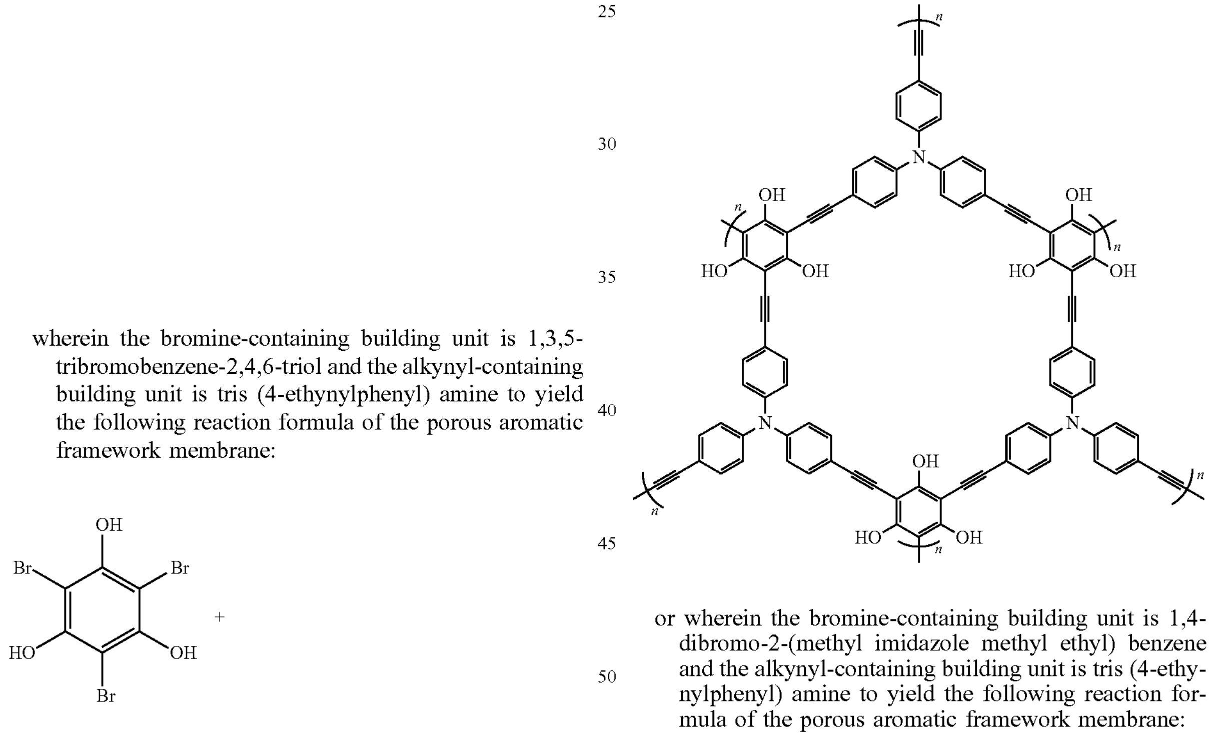

or wherein the bromine-containing building unit is 1,4-dibromo-2-(methyl imidazole methyl ethyl) benzene and the alkynyl-containing building unit is tris (4-ethynylphenyl) amine to yield the following reaction formula of the porous aromatic framework membrane:

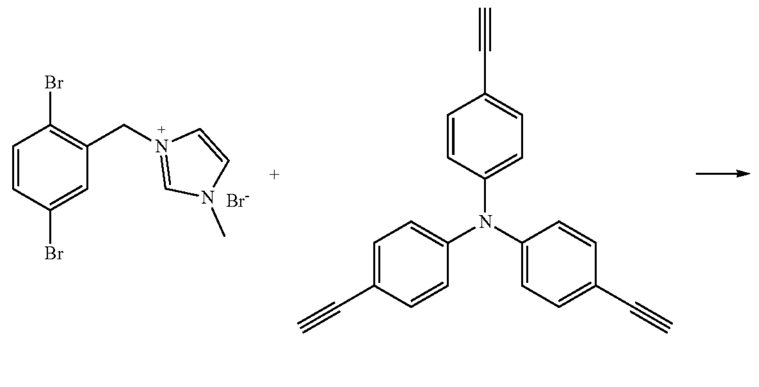

-continued

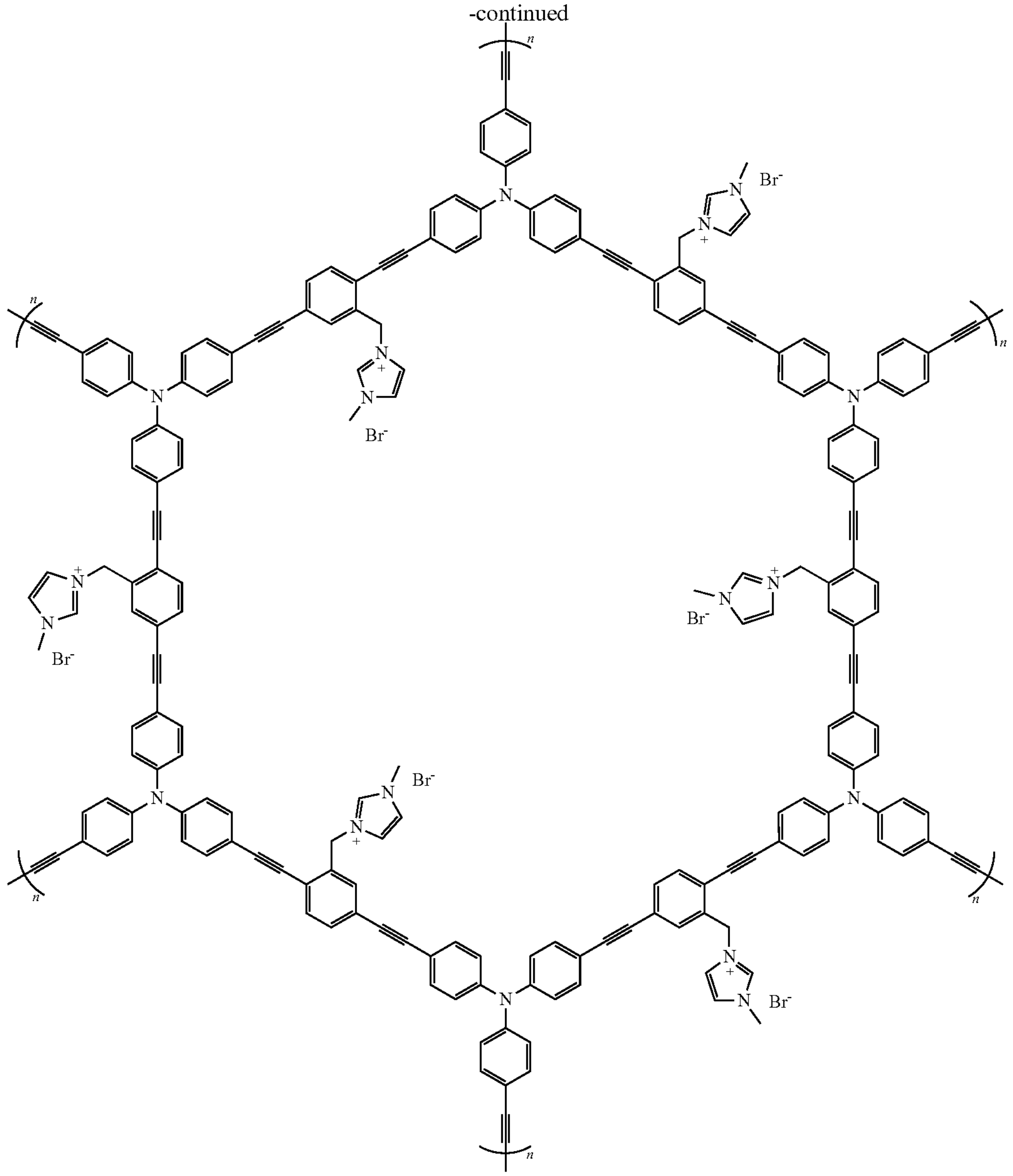

wherein, n≥1.

7. The method for preparing a porous aromatic framework membrane based on an inorganic salt template according to claim 1, wherein a ratio of an amount of the bromine-containing building unit to a volume of the triethylamine is 0.01 mmol: 10-40 mL.

8. The method for preparing a porous aromatic framework membrane based on an inorganic salt template according to claim 1, wherein the catalyst is composed of tetrakis (triphenylphosphine) palladium and cuprous iodide, and a mass ratio of the tetrakis (triphenylphosphine) palladium to the cuprous iodide is 10-15:2-5; and a ratio of an amount of the bromine-containing building unit to a mass of the tetrakis (triphenylphosphine) palladium is 0.01 mmol: 10-15 mg.

9. The method for preparing a porous aromatic framework membrane based on an inorganic salt template according to claim 1, wherein the pressure-assisted method comprises a suction filtration operation.

10. The method for preparing a porous aromatic framework membrane based on an inorganic salt template according to claim 1, wherein removing the inorganic salt comprises: washing the inorganic salt layer with chloroform, methanol, and water.

* * * * *